United States Patent [19]

Kimura et al.

[11] Patent Number: 5,785,767
[45] Date of Patent: Jul. 28, 1998

[54] CLEANING AND DISINFECTING SOLUTION FOR CONTACT LENS AND METHOD OF CLEANING AND DISINFECTING CONTACT LENS USING THE SOLUTION

[75] Inventors: Norio Kimura, Kasugai; Akira Nakagawa, Yokkaichi, both of Japan

[73] Assignee: Tomey Technology Corporation, Japan

[21] Appl. No.: 722,033

[22] PCT Filed: Feb. 19, 1996

[86] PCT No.: PCT/JP96/00359

§ 371 Date: Oct. 3, 1996

§ 102(e) Date: Oct. 3, 1996

[87] PCT Pub. No.: WO96/25957

PCT Pub. Date: Aug. 29, 1996

[30] Foreign Application Priority Data

Feb. 21, 1995 [JP] Japan ............... 7-032648

[51] Int. Cl.$^6$ ............... C11D 3/386; C11D 3/20; C11D 3/44; B08B 3/00
[52] U.S. Cl. ............... 134/42; 510/112; 510/113; 510/114; 510/115; 510/392; 510/530; 510/475
[58] Field of Search ............... 510/112, 113, 510/114, 115, 392, 530, 475; 435/263, 264; 134/42; 422/28

[56] References Cited

U.S. PATENT DOCUMENTS

| | | | |
|---|---|---|---|
| 3,910,296 | 10/1975 | Karageozian et al. | 134/2 |
| 4,614,549 | 9/1986 | Ogunbiyi et al. | 134/19 |
| 5,096,607 | 3/1992 | Mowrey-McKee et al. | 422/28 |
| 5,238,543 | 8/1993 | Carpenter et al. | 435/26.1 |
| 5,298,182 | 3/1994 | Tsao et al. | 510/112 |
| 5,314,823 | 5/1994 | Nakagawa et al. | 435/264 |
| 5,356,803 | 10/1994 | Carpenter et al. | 435/200 |
| 5,364,637 | 11/1994 | De et al. | 435/264 |
| 5,395,541 | 3/1995 | Carpenter | 510/363 |
| 5,411,598 | 5/1995 | Tsao et al. | 134/26 |
| 5,576,278 | 11/1996 | Van Duzee et al. | 510/114 |
| 5,604,190 | 2/1997 | Chowhan et al. | 510/114 |
| 5,605,661 | 2/1997 | Asgharian et al. | 422/28 |

FOREIGN PATENT DOCUMENTS

| | | |
|---|---|---|
| 1-180515 | 7/1989 | Japan . |
| 4-370197 | 12/1992 | Japan . |
| 6-95043 | 4/1994 | Japan . |

*Primary Examiner*—Kery A. Fries
*Attorney, Agent, or Firm*—Parkhurst & Wendel, L.L.P.

[57] ABSTRACT

It is an object of the present invention to provide a cleaning and disinfecting solution for a contact lens to be cleaned and disinfected simultaneously in a simplified manner with high efficiency. It is also an object of the present invention to provide a method of cleaning and disinfecting the contact lens wherein the cleaning and disinfection of the contact lens can be effected simultaneously in a short period of time by using the above-indicated cleaning and disinfecting solution. The above objects may be obtained according to one aspect of the present invention which provided a cleaning and disinfecting solution for a contact lens comprising an effective amount of proteolytic enzyme, 60–80% w/v % of propylene glycol, 10–35% w/v % of glycerine, and water, a total content of propylene glycol and glycerine being in the range of 70% to 95 w/v %. The latter object may be obtained according to another aspect of the invention which provides a method of simultaneously cleaning and disinfecting a contact lens by contacting the contact lens with the above-indicated contact lens cleaning and disinfecting solution for a short period of time of less than five minutes.

15 Claims, No Drawings

CLEANING AND DISINFECTING SOLUTION FOR CONTACT LENS AND METHOD OF CLEANING AND DISINFECTING CONTACT LENS USING THE SOLUTION

BACKGROUND OF THE INVENTION

1. Field of the Art

The present invention relates to a cleaning and disinfecting solution for a contact lens and a method of cleaning and disinfecting the contact lens using the solution.

2. Discussion of the Related Art

Generally, a contact lens is classified into a non-water contained contact lens, and a water-contained contact lens called as a soft contact lens. These contact lenses are likely to be soiled with deposits such as protein and lipid during wearing of the contact lenses on the eyes of the user, which deposits derive from tear fluid or lipid included in the tear fluid. These deposits adhering to the contact lenses deteriorate the wearing comfort of the contact lenses as felt by the user, and lower the eye sight of the user. In view of this, it is required to regularly clean the contact lens to remove the deposits therefrom for comfortable and proper wearing of the contact lenses on the user's eyes.

In a conventional method of cleaning the contact lens for removal of the deposits adhering to the contact lens, the lipid deposit is removed from the contact lens by rubbing the contact lens with a cleaning solution which includes a surface active agent, while the protein deposit is removed by immersing the contact lens in a cleaning solution which includes a proteolytic enzyme.

In general, bacteria or germs tend to adhere to, and proliferate on, the surfaces of the contact lens, especially the surfaces of the soft contact lens. In view of this, it is necessary to disinfect the contact lens on a regular basis for preventing the eyes of the lens wearer from being infected with the bacteria or germs.

For disinfecting the contact lens, there are conventionally known a heat disinfecting method in which the contact lens is heated, and a chemical disinfecting method which utilizes a chemical disinfectant such as hydrogen peroxide. In the heat disinfecting method, the contact lens is heated at a temperature higher than 80° C. by using a suitable boiling and disinfecting device, so that the contact lens is sterilized. This method requires one hour or more, including time required for elevating the temperature and cooling the contact lens. Thus, it takes a relatively long period of time to complete the disinfection of the contact lens. In the chemical disinfecting method using hydrogen peroxide, the contact lens is soaked in an aqueous solution of hydrogen peroxide so as to disinfect the contact lens. This chemical disinfecting method requires an additional treatment of neutralization after the disinfection of the contact lens, undesirably making the disinfecting method cumbersome and difficult. To solve this drawback, the disinfection and the neutralization may be effected in a single step using a catalyst, for example. However, this method is inconvenient since it also requires a relatively long period of time for the disinfection and neutralization. In the chemical disinfecting method, the chemical disinfectant exhibits only a small degree of sterilizing effect (disinfecting effect). Thus, the method inevitably requires four or more hours for the disinfection of the contact lens. In addition, the user may suffer from side effects such as allergy.

Generally, the contact lens is cleaned and disinfected in different steps. However, it would be more convenient to the contact lens user if the contact lens is cleaned and disinfected simultaneously in a simplified manner. Thus, there has been a demand for a method of simultaneously cleaning and disinfecting the contact lens. Laid-open Publication No. 2-289255 of unexamined Japanese patent application (see U.S. Pat. No. 5,096,607 to Mowrey-McKee et al.) discloses one example of such a method of simultaneously cleaning and disinfecting the contact lens wherein the contact lens is simultaneously cleaned and sterilized by immersing the contact lens in a composition which comprises a proteolytic enzyme and an antimicrobial agent and whose osmotic pressure is held at a level adjacent to a physiological state. This method was developed in view of a fact that the activity of the antimicrobial agent is not likely to be inhibited when a treatment liquid has the osmotic pressure value adjacent to the physiological state. Like the conventional chemical disinfecting method, this method also requires a relatively long period of time during which the contact lens is immersed in the above-described composition for cleaning and disinfecting the contact lens.

Another example of the method of simultaneously cleaning and disinfecting the contact lens is disclosed in laid-open Publication No. 2-240199 of unexamined Japanese patent application, wherein the contact lens is cleaned by rubbing with a cleaning and disinfecting composition for the contact lens which includes alkylene glycol such as propylene glycol, a lower alkanol such as ethanol, and a surface active agent. However, this composition is not effective to remove the protein deposit since it does not include the proteolytic enzyme. Even if this composition contains the proteolytic enzyme, the proteolytic enzyme is not stable in the composition, resulting in insufficient effect of removing the protein deposit. Accordingly, the contact lens needs to be cleaned in an additional step to remove the protein deposit, undesirably making the method cumbersome.

Laid-open Publication No. 1-180515 of unexamined Japanese Patent application discloses a contact lens cleaning solution which comprises an organic liquid miscible with water such as glycerine or propylene glycol, and the proteolytic enzyme. This publication also discloses a method of cleaning the contact lens by rubbing the contact lens with the cleaning solution so as to remove the protein deposit. In this cleaning solution, too, the proteolytic enzyme tends to be unstable depending upon the kind and combination of the organic liquid to be used, leading to insufficient cleaning effect of the cleaning solution. This cleaning solution may include a sterilizing agent or antiseptic agent for attaining the disinfecting effect. However, a sufficient disinfecting effect can not be obtained by simply rubbing the contact lens in a relatively short period of time. Thus, this method required an additional step of disinfecting the contact lens.

SUMMARY OF THE INVENTION

The present invention was developed in the light of the above-described situations. It is therefore an object of the invention to provide a cleaning and disinfecting solution for a contact lens which makes it possible to clean the contact lens for removal of the lipid and protein deposits adhering to the lens, and disinfect the contact lens, simultaneously in a simplified manner, while assuring easy handling of the contact lens. It is also an object of the invention to provide a method of cleaning and disinfecting the contact lens wherein the cleaning and disinfection of the contact lens can be simultaneously effected in a short period of time by using the contact lens cleaning and disinfecting solution as described above.

The inventors of the present invention have made an extensive study in an effort to solve the above-described problems, and found that the contact lens is effectively cleaned and disinfected at the same time by a combined use of propylene glycol and glycerine in the respective specific amounts, in the presence of a proteolytic enzyme. The present invention was developed based on the finding.

The above-indicated object may be attained according to one aspect of the present invention which provides a cleaning and disinfecting solution for a contact lens characterized by comprising an effective amount of a proteolytic enzyme, 60–80 w/v % of propylene glycol, 10–35 w/v % of glycerine, and water, a total content of the propylene glycol and the glycerine being in a range of 70–95 w/v %.

The contact lens cleaning and disinfecting solution according to the present invention includes 60–80 w/v % of propylene glycol and 10–35 w/v % of glycerine, together with the effective amount of proteolytic enzyme, and the total content of the propylene glycol and glycerine is held in a range of 70–95 w/v %, so that the proteolytic enzyme is advantageously stabilized, whereby the protein deposit is effectively removed from the contact lens.

In addition, the propylene glycol included in the solution for the purpose of stabilizing the proteolytic enzyme exhibits disinfecting effect and cleaning effect with respect to the lipid deposit. The propylene glycol exhibits the effects in a short time. Accordingly, the contact lens cleaning and disinfecting solution of the present invention exhibits excellent disinfecting effect as well as excellent cleaning effect.

According to one preferred form of the above aspect of the invention, the proteolytic enzyme is included in the cleaning and disinfecting solution in an amount of 0.1–10 w/v %.

According to another preferred form of the above aspect of the invention, the propylene glycol is included in an amount of 65–75 w/v % and the glycerine is included in an amount of 20–30 w/v %, the total content of the propylene glycol and the glycerine being in a range of 85–95 w/v %.

According to still another preferred form of the above aspect of the invention, pH of the cleaning and disinfecting solution is adjusted in a range of 5.0–9.5, and the cleaning and disinfecting solution further comprises 0.1–20 w/v % of a surface active agent.

According to a further preferred form of the above aspect of the invention, the proteolytic enzyme is serine protease, and the cleaning and disinfecting solution further comprises calcium ion in a concentration of 5–250 mM/l.

The latter object may be attained according to another aspect of the present invention which provides a method of simultaneously cleaning and disinfecting a contact lens. More specifically described, the aspect of the invention provides a method of cleaning and disinfecting a contact lens which is characterized by simultaneously cleaning and disinfecting the contact lens, comprising: preparing a cleaning and disinfecting solution for a contact lens which comprises an effective amount of proteolytic enzyme, 60–80 w/v % of propylene glycol, 10–35 w/v % of glycerine, and water, a total content of the propylene glycol and the glycerine being in a range of 70–95 w/v %; and contacting the contact lens with the cleaning and disinfecting solution for the contact lens for a short period of time of no more than five minutes.

According to the method of cleaning and disinfecting the contact lens of the present invention wherein the contact lens is cleaned and disinfected by using the contact lens cleaning and disinfecting solution, the contact lens is cleaned and disinfected at the same time. Further, since the propylene glycol exhibits the effects as described above in a short time, the contact lens can be effectively cleaned and disinfected even if the contact lens is kept in contact with the solution for the short period of time of no more than five minutes.

According to one preferred form of the above aspect of the invention, the proteolytic enzyme is included in the cleaning and disinfecting solution in an amount of 0.1–10 w/v %.

According to another preferred form of the above aspect of the invention, the propylene glycol is included in an amount of 65–75 w/v % and the glycerine is included in an amount of 20–30 w/v %, the total content of the propylene glycol and the glycerine being in a range of 85–95 w/v %.

According to still another preferred form of the above aspect of the invention, the pH of the cleaning and disinfecting solution is adjusted in a range of 5.0–9.5, and the cleaning and disinfecting solution further comprises 0.1–20 w/v % of a surface active agent.

In the present method of cleaning and disinfecting the contact lens using the above-described cleaning and disinfecting solution, when the serine protease is included in the solution as the proteolytic enzyme, calcium ion is preferably included in the solution in a concentration of 5–250 mM/l, in addition to the above-described components. The presence of the calcium ion is effective to stabilize the serine protease, leading to a high degree of cleaning effect or detergency with respect to the protein deposit.

Preferably, the present method of cleaning and disinfecting the contact lens further comprises: rinsing the contact lens with a physiological isotonic solution after the contact lens is contacted with the above-described cleaning and disinfecting solution; and immersing the contact lens in a fresh physiological isotonic solution. Further, the contacting the contact lens with the cleaning and disinfecting solution for the short period of time may be effected by rubbing the contact lens with the solution, resulting in improved cleaning effect.

DESCRIPTION OF THE PREFERRED EMBODIMENT

The proteolytic enzyme is generally classified, depending upon kinds of a residue in an active site thereof, into: serine protease; thiol protease; metal protease; and carboxyl protease. In particular, the serine protease and metal protease are preferably used as the proteolytic enzyme to be used in the present invention. This is because the serine protease and metal protease do not require any cofactor, to thereby assure easy handling thereof. On the other hand, the thiol protease and carboxyl protease need to be activated, making the handling cumbersome.

Described more specifically, when the serine protease and metal protease are used as the proteolytic enzyme, they effectively exhibit an enzyme activity without any cofactor. When the thiol protease is used as the proteolytic enzyme, it requires a suitable reducing agent as the cofactor. However, since the reducing agent is considerably unstable in an aqueous solution, the thiol protease is not likely to exhibit its effect to a satisfactory extent. When the carboxyl protease is used as the proteolytic enzyme, it is necessary to keep the cleaning and disinfecting solution acidic for permitting the carboxyl protease to exhibit a sufficient degree of the enzyme activity. However, in view of a fact that the contact lens cleaning and disinfecting solution may contact with fingers and eyes of the user, it is not desirable to keep the solution acidic since such an acidic solution may cause a high degree of irritation to the living body.

The metal protease suitably used as the proteolytic enzyme in the present cleaning and disinfecting solution has a metal such as zinc in its active site. Examples of the metal protease include collagenase and neutral protease which is derived form Bacillus. These enzymes are commercially available, such as "Thermolysin" from Wako Junyaku Kabushiki Kaisha, Japan and "HT-Proteolytic" from Kyowa-Solzyme K.K., Japan.

The serine protease includes a serine residue in its active site, and has an optimum pH ranging from neutral to alkaline. Since the serine protease does not require any cofactor such as the reducing agent, it is suitably employed in the present invention. Examples of the serine protease include trypsin, chymotrypsin derived from the animal, protease derived from the bacteria, actinomycetes and mold. Various kinds of the protease derived from Bacillus are commercially available, such as "BIOPRASE" from NAGASE SEIKAGAKU KOGYO K.K., Japan, "Subtilisin A" from Novo Industry, Japan, and "GL-440" from Kyowa-Solzyme K.K., Japan. The amount of the proteolytic enzyme such as the serine protease is suitably determined depending upon the cleaning effect or detergency to be exhibited by the proteolytic enzyme. The amount of the proteolytic enzyme is generally in a range of 0.1–10 w/v %, preferably 0.5–5 w/v %.

The serine protease derived from Bacillus has portions in the molecule adapted to bond with calcium ion. With the calcium ion being bonded to the portions as described above, the enzyme has a stable molecular structure. When the serine protease derived from Bacillus is used as the proteolytic enzyme, the calcium ion is added to the cleaning and disinfecting solution for increasing the stability of the proteolytic enzyme. Accordingly, the contact lens cleaning and disinfecting solution of the present invention effectively assures improved detergency with respect to the protein deposit.

The calcium ion is generally provided in the form of a calcium salt which generally has good water solubility, such as calcium chloride, calcium sulfate or calcium acetate. The calcium salt is added as the calcium ion to the cleaning and disinfecting solution in a concentration of 5–250 mM/l. For instance, salt of calcium chloride dihydrates is added generally in an amount of 0.1–3.0 w/v % (in a concentration of 6.8–204 mM/l), preferably in an amount of 0.3–1.5 w/v % (in a concentration of 20.4–102 mM/l). If the concentration of the calcium ion is lower than 5 mM/l, the calcium ion does not exhibit sufficient effect of stabilizing the enzyme. On the other hand, the enzyme stabilizing effect does not significantly increase with an increase in the concentration of the calcium ion above 250 mM/l.

The contact lens cleaning and disinfecting solution according to the present invention employs, as a solvent, a mixed solvent wherein the glycerine and propylene glycol are mixed in water in the respective proportions. The glycerine and propylene glycol have a function to stabilize the proteolytic enzyme so that the proteolytic enzyme is stable, to thereby assure improved cleaning effect with respect to the protein deposit.

The propylene glycol does not only stabilize the proteolytic enzyme, but also exhibits excellent sterilizing or disinfecting effect and cleaning effect for removal of the lipid deposit. Accordingly, the present contact lens cleaning and disinfecting solution is capable of effectively exhibiting excellent lipid-deposit removal effect and excellent disinfecting effect, in addition to the cleaning effect exhibited by the proteolytic enzyme.

When it is desired to disinfect the contact lens in a relatively short time, the sterilizing agent (disinfectant) is usually employed. Examples of such a disinfectant include: lower alcohol such as ethanol or propanol; alkylene glycol such as ethylene glycol or propylene glycol; biguanides such as chlorhexidine gluconate; and quaternary ammonium salts. However, there are some restrictions in selecting the disinfectant to be used for disinfecting the contact lens. Namely, it is necessary to consider an influence of the disinfectant on the stability of the proteolytic enzyme and the material of the contact lens. If the lower alcohol is employed as the disinfectant, for instance, the stability of the proteolytic enzyme is deteriorated and the material of the contact lens is considerably influenced when the concentration of the lower alcohol is held in a range wherein it exhibits a sufficient sterilizing (or disinfecting) effect.

In contrast, the propylene glycol used in the present invention exhibits a high degree of sterilizing effect and cleaning effect with respect to the lipid deposit, without adversely influencing the material of the contact lens. Further, the propylene glycol does not lower the stability of the proteolytic enzyme. Thus, the use of the propylene glycol is effective to solve the above-described problem.

The glycerine used in the present cleaning and disinfecting solution together with the propylene glycol is effective to further improve the effect of stabilizing the proteolytic enzyme and the effect of sterilization exhibited by the propylene glycol. Thus, the use of the glycerine together with the propylene glycol in the respective predetermined proportions assures further improved protein-deposit removal effect and disinfecting effect of the contact lens cleaning and disinfecting solution.

The present cleaning and disinfecting solution includes, as the disinfectant, the predetermined amount of propylene glycol, taking account of the influence on the stability of the proteolytic enzyme and the material of the contact lens. The present cleaning and disinfecting solution further includes the predetermined amount of glycerine for the purpose of improving the effects to be exhibited by the propylene glycol. Accordingly, the contact lens cleaning and disinfecting solution of the present invention assures excellent cleaning and disinfecting effects which were not obtained by the conventional cleaning and disinfecting solution.

For permitting the contact lens cleaning and disinfecting solution of the present invention to exhibit the excellent effects as described above, the propylene glycol is included in the solution in an amount of 60–80 w/v %, preferably in an amount of 65–75 w/v %. The cleaning and disinfecting solution does not exhibit a satisfactory sterilizing effect when the amount of the propylene glycol is smaller than 60 w/v %, while the stability of the proteolytic enzyme is deteriorated when the amount of the propylene glycol is larger than 80 w/v %.

The glycerine is included in the cleaning and disinfecting solution in an amount of 10–35 w/v %, preferably in an amount of 20–30 w/v %. If the amount of the glycerine is smaller than 10 w/v %, the proteolytic enzyme needs to be stabilized by the propylene glycol alone, leading to insufficient stabilization of the enzyme. On the other hand, the inclusion of the glycerine in an amount exceeding 35 w/v % may deteriorate the solubility of the other components.

The total content of the propylene glycol and the glycerine is generally in a range of 70–95 w/v %, preferably 85–95 w/v %. If the total content is smaller than 70 w/v %, the cleaning and disinfecting solution does not exhibit a sufficient sterilizing effect. The sterilizing effect does not increase with an increase in the total content of the propylene glycol and glycerine above 95 w/v %. On the other hand, the total content exceeding 95 w/v % may even deteriorate the solubility of the other components.

The present contact lens cleaning and disinfecting solution has a pH value usually in a range of 5.0–9.5, preferably 5.5–7.5. When the pH of the cleaning and disinfecting solution is lower than 5.0, the stability of the proteolytic enzyme is deteriorated, leading to insufficient cleaning effect. If the pH of the cleaning and disinfecting solution is higher than 9.5, it would cause irritation and harm to the eye and the skin of the user, and give an adverse influence on the material of the contact lens. For adjusting the pH of the cleaning and disinfecting solution in a range of 5.0–9.5, a suitable buffer is added to the cleaning and disinfecting solution as needed.

The buffer to be added to the solution is suitably selected from among various known buffers which do not deteriorate the stability of the proteolytic enzyme. When the serine protease is used as the proteolytic enzyme and the calcium ion is added to the solution for stabilizing the serine protease, a suitable buffer is selected which does not cause precipitation in the cleaning and disinfecting solution due to interaction of the calcium ion and the buffer. Examples of such buffer include a buffer comprising tris(hydroxymethyl) aminomethane and hydrochloric acid, and a buffer comprising boric acid and/or borax. In the present invention, the buffer comprising boric acid and/or borax is preferably employed. The buffer is included in the cleaning and disinfecting solution in an amount of about 0.1–10 w/v %. If the amount of the buffer is smaller than 0.1 w/v %, the buffer is not likely to exhibit its effect, deteriorating the pH stability. On the other hand, the pH stability does not increase with an increase in the amount of the buffer larger than 10 w/v %.

The present cleaning and disinfecting solution for the contact lens may include various known surface active agents, for improving the cleaning effect with respect to the lipid deposit derived from lipid in the tear fluid and adhering to the contact lens, and for increasing the viscosity of the cleaning and disinfecting solution. It is desirable to select the surface active agent which assures a high degree of safety with respect to the living body without adversely influencing the material of the contact lens and deteriorating the stability of the proteolytic enzyme. One example of such surface active agent is a nonionic surface active agent, such as polyoxyethylene-polyoxypropylene block copolymer, condensation product of polyoxyethylene and ethylenediamine, fatty acid glyceryl ester, alkanoic acid sucrose ester, polyoxyethylene alkylamine, sorbitan fatty acid polyoxyethylene ester. In particular, polyoxyethylene-polyoxypropylene block copolymer is preferably employed in the present invention. The surface active agent is included in the cleaning and disinfecting solution generally in an amount of 0.1–20 w/v %, preferably 0.5–10 w/v %.

The cleaning and disinfecting solution for the contact lens according to the present invention is obtained by dissolving the proteolytic enzyme, and the buffer or the surface active agent as needed, in a mixed solvent consisting of water, glycerine having a predetermined concentration and propylene glycol having a predetermined concentration.

In the method of cleaning and disinfecting the contact lens according to the present invention, the contact lens is kept in contact with the above-described cleaning and disinfecting solution for a relatively short period of time of no more than five minutes. The present method enables the contact lens to be simultaneously and simply cleaned and disinfected in a short period of time.

Described more specifically, several droplets of the cleaning and disinfecting solution are applied to the contact lens which was removed from the eye of the user. The contact lens is cleaned by rubbing for 20–30 seconds with the lens being gripped between the user's thumb and forefinger, or with the lens being held on his/her palm. Subsequently, the contact lens is rinsed with a physiological isotonic solution and then, the lens is immersed in a fresh physiological isotonic solution for several minutes. Thus, a sequence of the procedure of cleaning and disinfecting the contact lens is completed. Any known physiological isotonic solution may be employed, provided that the physiological isotonic solution has an osmotic pressure value generally in a range of 150–400 mOsm, preferably 200–350 mOsm, and assures a high degree of safety with respect to the living body without adversely influencing the contact lens material.

The lipid and protein deposits adhering to the contact lens can be effectively cleaned and removed in a short period of time by the above-described procedure according to the present invention. In the present method, the contact lens can be cleaned and disinfected at the same time in a simplified manner, eliminating cumbersome procedure as required in the conventional method.

EXAMPLES

To further clarify the concept of the present invention, some examples of the invention will be described. It is to be understood, however, that the present invention is not limited to the details of the illustrated examples, but may be modified with various changes, modifications and improvements, which may occur to those skilled in the art without departing from the spirit of the present invention.

Example 1

A specimen No. 1 of the cleaning and disinfecting solution for the contact lens according to the present invention was prepared in the following manner, so that the specimen No. 1 has the composition as indicated in TABLE 1. Initially, 1 mL of purified water was added to 0.5 g of Calcium Chloride (available from Tomida Pharmaceutical Co., Ltd. Japan). To this mixture, there were added 30 g of Glycerine (available from Nippon Oil and Fats Co., Ltd., Japan) and 65 g of Propylene Glycol (available from Wako Junyaku Kogyo Kabushiki Kaisha, Japan). Further, 0.6 g of a proteolytic enzyme derived from Bacillus ("SP-614" available from Novo Industry, Japan), 5 g of polyoxyethylene-polyoxypropylene block copolymer as the nonionic surface active agent ("Pluronic L-64" available from ASAHI DENKA KOGYO K.K., Japan) and 1.0 g of Sodium Borate as the buffer (available from Tomida Pharmaceutical Co., Ltd, Japan) were dissolved in the mixture. To the thus obtained solution, there was added purified water so that the solution had a total volume of 100 mL. Then, the solution was adjusted of its pH to 6.0 with 2.5N aqueous solution of sodium hydroxide, whereby the specimen No. 1 of the cleaning and disinfecting solution was obtained.

In the same manner as the specimen No. 1 of the present cleaning and disinfecting solution, specimens Nos. 2 and 3 of the present cleaning and disinfecting solution and specimens Nos. 1 and 2 of the cleaning and disinfecting solution as comparative examples were prepared, so that these specimens have the respective compositions as shown in TABLE 1.

TABLE 1

| components | Present Invention | | | Comparative Examples | |
|---|---|---|---|---|---|
| | 1 | 2 | 3 | 1 | 2 |
| propylene glycol | 65 | 65 | 75 | 65 | 85 |
| glycerine | 30 | 30 | 20 | — | 10 |
| 2-propanol | — | — | — | 13.5 | — |
| proteolytic enzyme | 0.6 | 0.5 | 0.6 | 0.6 | 0.6 |
| calcium chloride dihydrates | 0.5 | 0.8 | 0.8 | 0.5 | 0.5 |
| nonionic surface active agent | 5.0 | 0.5 | 1.0 | 5.0 | 5.0 |
| sodium borate | 1.0 | 2.5 | 1.0 | 1.0 | 1.0 |

(unit: g)

As in the specimen No.1 of the present invention, the proteolytic enzyme derived from Bacillus: SP-614 (available from Novo Industry, Japan) was used in the specimen No. 3 of the present invention and the specimens Nos. 1 and 2 of the comparative examples. In the specimen No. 2 of the present invention, the proteolytic enzyme derived from Bacillus: Clear Lens Pro 2.5MG (available from Novo Industry, Japan) was used. As the nonionic surface active agent, polyoxyethylene-polyoxypropylene block copolymer (Pluronic L-64) was used in the specimen No. 3 of the present invention and the specimens Nos. 1 and 2 of the comparative examples, while polyoxyethylene-polyoxypropylene block copolymer ("Lutrol F127" available from BASF, Germany) was used in the specimen No. 2 of the present invention. In the specimen No. 1 of the comparative examples, 0.9 g of sodium chloride and 0.1 g of hydroxyethyl cellulose were added in addition to the components as described above.

<Enzyme Stability Test>

For each of the specimens Nos. 1–3 of the cleaning and disinfecting solution according to the present invention and each of the specimens Nos. 1 and 2 of the cleaning and disinfecting solution according to the comparative examples, there were measured, in the following manner, enzyme activity upon preparation of each specimen of the cleaning and disinfecting solution, and residual enzyme activity after each specimen was stored at the temperature of 60° C. for one week.

Initially, each specimen of the cleaning and disinfecting solution was diluted with purified water at a suitable dilution ratio "d". To 1 mL of each diluted specimen of the cleaning and disinfecting solution, protein in the form of 0.6 w/v % aqueous solution of casein (pH 7.00, 0.05M aqueous solution of sodium monohydrogenphosphate) was added in an amount of 5 mL while it was kept at 37° C. The thus obtained mixture was kept at 37° C. for 10 minutes, so that the protein was processed by the proteolytic enzyme included in each specimen of the cleaning and disinfecting solution. Subsequently, 5 mL of precipitant (i.e., a mixed solution consisting of 0.11M trichloroacetic acid, 0.22M sodium acetate and 0.33M acetic acid) was added to the above mixture, whereby undecomposed protein was precipitated. Then, the mixture was subjected to filtration, and the filtrate was measured of its absorbance (A) at 275 nm. As control experiments, each specimen of the cleaning and disinfecting solution was diluted with purified water at the dilution ratio "d". To 1 mL of each diluted specimen of the cleaning and disinfecting solution, 5 mL of the above-indicated precipitant was added. Further, 5 mL of the above-indicated aqueous solution of casein was added, so that the protein was precipitated. The mixture was subjected to filtration, and the filtrate was measured of its absorbance ($A_0$) at 275 nm. The activity of the proteolytic enzyme was calculated from the following equation based on the results of measurement. The activity of the proteolytic enzyme is defined as 1 unit when the enzyme activity is capable of producing, for one minute, non-protein material that provides absorbance corresponding to an amount of $1 \times 10^{-6}$ of tyrosine at 275 nm.

Proteolytic enzyme activity (unit/mL) =

$$\{(A - A_0)/(A_s/50)\} \times 11 \times d/10$$

wherein $A_s$: absorbance of 50 μg of tyrosine at 275 nm
= 0.391 d: dilution ratio

The residual activity was calculated from the following equation, on the basis of the proteolytic enzyme activity measured upon preparation of each specimen of the cleaning and disinfecting solution and the proteolytic enzyme activity measured after each specimen of the cleaning and disinfecting solution was stored at 60° C. for one week, according to the above equation.

Residual activity (%) = {(the proteolytic enzyme activity after storage at 60° C. for one week)/(the proteolytic enzyme activity upon preparation)} × 100

TABLE 2

| | | enzyme activity upon preparation (unit/mL) | enzyme activity after one week (unit/mL) | residual enzyme activity (%) |
|---|---|---|---|---|
| Present Invention | 1 | 1158 | 1005 | 87 |
| | 2 | 1167 | 937 | 80 |
| | 3 | 1125 | 987 | 88 |
| Comparative Examples | 1 | 1035 | 50 | 5 |
| | 2 | 1132 | 464 | 41 |

It was confirmed from the results of TABLE 2 that the cleaning and disinfecting solution for the contact lens according to the present invention exhibited excellent enzyme stability. In contrast, it was recognized that the cleaning and disinfecting solution according to the comparative examples did not exhibit sufficient enzyme stability.

Example 2

The contact lens cleaning and disinfecting solution according to the present invention was examined of its inhibitory effect on development of bacteria or fungi in order to confirm the disinfecting effect exhibited by the cleaning and disinfecting solution.

Initially, there were prepared the specimens Nos. 1–3 of the cleaning and disinfecting solution according to the present invention as used in the Example 1. Further, there were prepared specimens Nos. 3 through 7 of the cleaning and disinfecting solution as comparative examples, so that the specimens Nos. 3–7 have the respective compositions as indicated in TABLE 3.

TABLE 3

| components | Comparative Examples | | | | |
|---|---|---|---|---|---|
|  | 3 | 4 | 5 | 6 | 7 |
| propylene glycol | 35 | 55 | — | — | — |
| glycerine | 60 | 30 | 95 | 55 | 60 |
| diethylene glycol | — | — | — | 30 | — |
| proteolytic enzyme | 0.6 | 0.6 | 0.6 | 0.6 | 0.6 |
| calcium chloride dihydrates | 0.5 | 0.5 | 0.5 | 0.5 | 0.5 |
| nonionic surface active agent | 5.0 | 5.0 | 5.0 | 5.0 | 5.0 |
| sodium borate | 1.0 | 1.0 | 1.0 | 1.0 | 1.0 |

(unit: g)

As in Example 1, in these specimens Nos. 3–7 of the comparative examples, the proteolytic enzyme derived from Bacillus: SP-614 (available from Novo Industry, Japan) was used while polyoxyethylene-polyoxypropylene block copolymer (Pluronic L-64) was used as the nonionic surface active agent. In the cleaning and disinfecting solution of the specimen No. 7, 0.5 g of potassium sorbate was added as the antiseptic agent, in addition to the components as indicated in TABLE 3.

Next, 28.5 g of Glucose Peptone Agar for the sterility test (available from EIKEN CHEMICAL CO., LTD., Japan) and 15 g of agar powder for bacteria medium (available from Wako Junyaku Kogyo Kabushiki Kaisha, Japan) were dissolved in 1000 mL of distilled water. This mixture was subjected to steam sterilization under high pressure at 121° C. for 20 minutes, whereby Glucose Peptone agar medium was prepared. In the meantime, 40.0 g of Tryptone Soya Agar (available from EIKEN CHEMICAL CO., LTD., Japan) was dissolved in 1000 mL of distilled water. This mixture was subjected to steam sterilization under high pressure at 121° C. for 20 minutes, whereby Tryptone Soya Agar medium was prepared.

10 mL of the specimens Nos. 1–3 of the cleaning and disinfecting solution according to the present invention and the specimens Nos. 3–7 of the cleaning and disinfecting solution according to the comparative examples were poured into the respective test tubes. To each of the test tubes, there was added 0.01 mL of fungi liquid comprising *Candida albicans* ATCC 10231 in an amount of $10^6$CFU/mL-$10^9$CFU/mL. The mixture was stirred, and adjusted so as to contain the *Candida albicans* ATCC 10231 in an amount of $10^6$CFU/mL-$10^7$CFU/mL. Thereafter, the mixture was left at room temperature for five minutes. (Hereinafter, this mixture is referred to as "fungi suspension"). Then, 1 mL of the fungi suspension was taken out from each of the test tubes, and was diluted every 10 times with a physiological salt solution, so as to provide samples having different numbers of the fungi. Each of the thus obtained samples was cultured using 20 mL of the Glucose Peptone agar medium, and was measured of its viable cell count per 1 mL by plate dilution method. On the basis of the obtained value, the viable cell count per 1 mL of each fungi suspension was calculated. The results are indicated in TABLE 4. The viable cell count was measured by the plate dilution method, using the samples wherein colonies were suitably dispersed on the plate after culture, and the development of the fungi was not inhibited.

In the same manner as described above, bacteria suspensions comprising *Staphylococcus aureus* ATCC 6538P were prepared, and the viable cell count was measured for each of the bacteria suspensions. The results of the measurement are also indicated in TABLE 4. For cultivation of samples, 17 mL of Tryptone Soya agar medium was employed in place of 20 mL of Glucose Peptone agar medium as used above.

TABLE 4

| bacteria or fungi | Present Invention | | | Comparative Examples | | | | |
|---|---|---|---|---|---|---|---|---|
|  | 1 | 2 | 3 | 3 | 4 | 5 | 6 | 7 |
| C.A. | 100 | 100 | 10 | $10^6$ | $10^6$ | $10^6$ | $10^6$ | $10^6$ |
| S.A. | less than 10 | less than 10 | less than 10 | $10^5$ | $10^5$ | $10^6$ | $10^6$ | $10^6$ |

C.A.: *Candida albicans*
S.A.: *Staphylococcus aureus*

It was confirmed from the results of TABLE 4 that the cleaning and disinfecting solution for the contact lens according to the present invention exhibited excellent disinfecting effect. The conventional cleaning and disinfecting solution (the specimen No. 6 of the comparative examples) did not show sufficient disinfecting effect, even though the solution employed, in addition to the antiseptic agent, a combination of glycerine and diethylene glycol which was considered effective for stabilizing the enzyme.

Example 3

In the above EXAMPLE 2, the disinfecting effect of the cleaning and disinfecting solution was confirmed by reacting the solution with the suspension of microorganisms. In this EXAMPLE 3, the cleaning and disinfecting solution was examined of the disinfecting effect using contact lenses.

There were prepared two soft contact lenses ("MENICON SOFT 72" available from Menicon Co., Ltd, Japan), contact lens holders for receiving the respective contact lenses and containers for accommodating the respective holders and rinsing liquid.

Next, a fungi solution was prepared which included a kind of mold, i.e., *Aspergillus fumigatus* ATCC 10894, in an amount of $10^8$CFU/mL-$10^9$CFU/mL. The surfaces of the contact lenses were uniformly coated with 0.02 mL of the thus prepared fungi solution, and the contact lenses were kept at room temperature for 10 minutes, so that the fungi adhered to the lens surfaces. To one of the contact lenses, 10 droplets of the cleaning and disinfecting solution of the specimen No.1 according to the present invention were applied with the contact lens being put on a palm, and the contact lens was cleaned by finger-rubbing for 30 seconds. To the other contact lens, 10 droplets of a sterile physiological salt solution were applied with the contact lens being put on a palm. This contact lens was also cleaned by finger-rubbing for 30 seconds.

After the contact lenses were fully rinsed with a physiological salt solution, they were put into the respective lens holders, and were immersed in 7 mL of a physiological salt solution (immersing liquid) in the respective containers. After 2 minutes, each contact lens and the whole amount of each immersing liquid were cultured in Glucose Peptone medium. The culture was effected at the temperature of 23° C. for 14 days. After the culture, each medium was observed for the presence of turbidity which is caused by proliferation of the fungi. The result showed that the fungi were not found in the medium wherein the contact lens treated by the cleaning and disinfecting solution of the specimen No. 1 of the present invention and its immersing liquid were cultured. On the contrary, the proliferation of the fungi was confirmed in the medium wherein the contact lens treated by the axenic physiological salt solution and its immersing liquid were cultured. It will be apparent from the results that the cleaning and disinfecting solution for the contact lens according to the present invention is capable of exhibiting excellent disinfecting effect when used in cleaning and disinfecting the contact lenses.

Example 4

<Test for Observing the Influence on the Size of the Contact Lens>

The present cleaning and disinfecting solution was observed for its influence on the size of the contact lens. Initially, 3 mL of the specimens Nos. 1-3 of the cleaning and disinfecting solution of the present invention were prepared. In the meantime, there were prepared three soft contact lenses ("MENICON SOFT 72" available from Menicon CO., Ltd, Japan). The diameter of each of the three contact lenses was measured in a physiological salt solution whose temperature was kept at 20° C. The three contact lenses were respectively immersed in the above-prepared specimens Nos. 1-3 of the cleaning and disinfecting solution, and kept at room temperature for 6 hours. After the contact lenses were fully rinsed with the physiological salt solution, they were immersed in 10 mL of the physiological salt solution for more than 5 minutes. Then, the diameter of each of the contact lenses was measured in the physiological salt solution of 20° C. The change in the diameter of each contact lens was calculated on the basis of the measured diameter value and the diameter value measured before the immersion in the cleaning and disinfecting solution. The results are indicated in the following TABLE 5.

TABLE 5

|  |  | cleaning and disinfecting solution Present Invention | | |
|---|---|---|---|---|
|  |  | 1 | 2 | 3 |
| diameter of contact lens | before immersion in the solution (mm) | 14.15 | 14.10 | 14.10 |
|  | after immersion in the solution (mm) | 14.35 | 14.25 | 14.20 |
|  | change in the diameter value (mm) | +0.20 | +0.15 | +0.10 |

As is apparent from the results of TABLE 5, the diameter values of the contact lenses did not substantially change even under a severe condition of 6-hour immersion in the cleaning and disinfecting solution. In other words, it was confirmed that the cleaning and disinfecting solution for the contact lens according to the present invention did not give substantial influence on the size of the contact lens.

Example 5

<Cleaning Effect Test with Respect to Lipid Deposit>

There was prepared an artificial lipid deposit 0composition as specified in ISO/TC 172/SC 7/WG 5 N 35, which gives the contact lens an artificial lipid deposit. This composition includes: 6 g of Arlacel 80; 16 g of castor oil, 35 g of lanolin; 5 g of oleic acid; 4 g of SPAN 85; 2 g of cetyl alcohol; 2 g of cholesterol; and 30 g of cholesterol acetate. These reagents are all available from Wako Junyaku Kogyo Kabushiki Kaisha, Japan.

Next, there were prepared four soft contact lenses ("MENICON SOFT 72" available from Menicon CO., Ltd, Japan). Each of the four contact lenses was uniformly coated with 0.1 g of the artificial lipid deposit composition prepared as described above.

One of the four contact lenses was put on a palm, and the cleaning and disinfecting solution of the specimen No. 1 according to the present invention was dropped on the contact lens. The contact lens was cleaned and disinfected by finger-rubbing for 30 seconds. After the cleaning and disinfecting treatment, the contact lens was rinsed with the physiological salt solution. Then, the contact lens was observed for its appearance, and it was confirmed that the artificial lipid deposit adhering to the contact lens was completely removed.

The cleaning and disinfecting solutions of the specimens Nos. 2 and 3 according to the present invention were examined for the lipid-deposit cleaning effect using two contact lenses, in the same manner as described above. It was confirmed that the artificial lipid deposit was completely removed from both of the contact lenses.

The last one of the four contact lenses was cleaned and disinfected in the same manner as described above, except that the physiological salt solution was used in place of the specimen No. 1 of the cleaning and disinfecting solution of the present invention. The contact lens was observed for its appearance, and it was found that the artificial lipid deposit adhering to the contact lens remained on the lens surfaces without being completely removed.

Example 6

<Cleaning Effect Test with Respect to Protein Deposit>

There was prepared a protein-contaminated liquid in the form of artificial tear fluid (pH 7.4), which includes: 0.388 g of albumin; 0.161 g of γ-globulin; 0.120 g of lysozyme; 0.900 g of sodium chloride; 0.015 g of calcium chloride (dehydrates); 0.104 g of sodium dihydrogenphosphate (dihydrates); 5 mL of 1N aqueous solution of sodium hydroxide; and 100 mL of purified water. Among these reagents, γ-globulin was available from SIGMA, Japan while the others were available from Wako Junyaku Kogyo Kabushiki Kaisha, Japan.

Four soft contact lenses ("MENICON SOFT MA" available from Menicon Co., Ltd, Japan) were prepared. These contact lenses were boiled in 1.5 mL of the artificial tear fluid for 30 minutes, and immersed in cool water for 30 minutes. This operation was repeated five times. After the treatment, the contact lenses were observed in the physiological salt solution by a dark-field microscope of 20× magnification, and it was confirmed that the entire surfaces of all of the contact lenses were soiled with white protein deposit.

One of the four contact lenses soiled with the protein deposit was put on a palm, and 0.5 mL of the specimen No. 1 of the cleaning and disinfecting solution according to the present invention was dropped on the contact lens. After the contact lens was lightly cleaned by rubbing between a thumb and a forefinger for 30 seconds, it was rinsed with the physiological salt solution, and immersed in 7 mL of the physiological salt solution for 2 minutes. This operation was repeated 30 times. Thereafter, the contact lens was observed in 20× magnification, and it was confirmed that the protein deposit was completely removed from the contact lens.

The specimens Nos. 2 and 3 of the cleaning and disinfecting solution according to the present invention were examined for the protein-deposit cleaning effect using two contact lenses, in the same manner as described above. It was confirmed that the protein deposit was completely removed from both of the contact lenses.

The last one of the four contact lenses was treated in the same manner as described above, except that a commercially available cleaning solution ("MENICLEAN" available from Menicon CO., Ltd, Japan) was employed in place of the cleaning and disinfecting solution of the present invention. The contact lens was observed in 20× magnification, and it was found that the white protein deposit adhering to the entire surfaces of the contact lens remained without being completely removed from the lens surfaces.

Example 7

<Cleaning Effect Test with Respect to Protein Deposit>

There were prepared four hard contact lenses having a high degree of oxygen permeability ("MENICON SUPER EX" available from Menicon Co., Ltd, Japan). These contact lenses were boiled for 30 minutes in 1.5 mL of the artificial tear fluid as prepared in EXAMPLE 6, and immersed in cool water for 30 minutes. Thereafter, the contact lenses were observed by the dark-field microscope of 20× magnification, and it was confirmed that the entire surfaces of all of the contact lenses were soiled with white protein deposit.

One of the four contact lenses soiled with the protein deposit was put on a palm, and 0.5 mL of the specimen No. 1 of the cleaning and disinfecting solution according to the present invention was dropped on the contact lens. Then, the contact lens was lightly cleaned by rubbing between a thumb and a forefinger for 30 seconds. Thereafter, the contact lens was observed in 20× magnification, and it was confirmed that the protein deposit was completely removed from the contact lens.

The specimens Nos. 2 and 3 of the cleaning and disinfecting solution according to the present invention were examined for the protein-deposit cleaning effect using two contact lenses, in the same manner as described above. It was confirmed that the protein deposit was completely removed from both of the contact lenses.

The last one of the four contact lenses was treated in the same manner as described above, except that a commercially available cleaning solution ("O$_2$ CARE" available from Menicon CO., Ltd, Japan) was employed in place of the cleaning and disinfecting solution according to the present invention. The contact lens was observed in 20× magnification, and it was found that the white protein deposit adhering to the entire surfaces of the contact lens remained without being completely removed from the lens surfaces.

As is apparent from the results of Examples 5–7 that the cleaning and disinfecting solution for the contact lens according to the present invention exhibited, in a relatively short period of time, an excellent cleaning effect with respect to the lipid deposit and protein deposit which may adhere to the contact lenses.

Industrial Utility

It will be understood from the above description that the present invention provides the cleaning and disinfecting solution for the contact lens which permits easy and efficient cleaning and disinfecting of the contact lens. The present invention also provides the method of cleaning and disinfecting the contact lens wherein the contact lens is simultaneously cleaned and disinfected by using the above-described cleaning and disinfecting solution.

What is claimed is:

1. A cleaning and disinfecting solution for a contact lens which is characterized by comprising a protein stain-removing effective amount of a proteolytic enzyme, 60–80 w/v % of propylene glycol, 10–35 w/v % of glycerine, and water, a total content of said propylene glycol and said glycerine being in a range of 70–95 w/v %.

2. A cleaning and disinfecting solution for a contact lens according to claim 1, wherein said proteolytic enzyme is included in said cleaning and disinfecting solution in an amount of 0.1–10 w/v %.

3. A cleaning and disinfecting solution according to claim 1, wherein said propylene glycol is included in an amount of 65–75 w/v % and said glycerine is included in an amount of 20–30 w/v %, said total content of said propylene glycol and said glycerine being in a range of 85–95 w/v %.

4. A cleaning and disinfecting solution according to claim 1, wherein pH of said cleaning and disinfecting solution is adjusted in a range of 5.0–9.5.

5. A cleaning and disinfecting solution according to claim 1, a surface active agent is further included in an amount of 0.1–20 w/v %.

6. A cleaning and disinfecting solution according to claim 1, wherein said proteolytic enzyme is serine protease, and calcium ion is further included in a concentration of 5–250 mM/l.

7. A method of cleaning and disinfecting a contact lens characterized by simultaneously cleaning and disinfecting said contact lens, comprising: preparing a cleaning and disinfecting solution for a contact lens which comprises a protein stain-removing effective amount of proteolytic enzyme, 60–80 w/v % of propylene glycol, 10–35 w/v % of glycerine, and water, a total content of said propylene glycol and said glycerine being in a range of 70–95 w/v %; and contacting said contact lens with said cleaning and disinfecting solution for the contact lens for a short period of time of no more than five minutes.

8. A method of cleaning and disinfecting a contact lens according to claim 7, wherein said proteolytic enzyme is included in said cleaning and disinfecting solution in an amount of 0.1–10 w/v %.

9. A method of cleaning and disinfecting a contact lens according to claim 7, wherein said propylene glycol is included in an amount of 65–75 w/v % and said glycerine is included in an amount of 20–30 w/v %, said total content of said propylene glycol and said glycerine being in a range of 85–95 w/v %.

10. A method of cleaning and disinfecting a contact lens according to claim 7, wherein pH of said cleaning and disinfecting solution is adjusted in a range of 5.0–9.5.

11. A method of cleaning and disinfecting a contact lens according to claim 7, wherein said cleaning and disinfecting solution further comprises a surface active agent in an amount of 0.1–20 w/v %.

12. A method of cleaning and disinfecting a contact lens according to claim 7, wherein said cleaning and disinfecting solution includes serine protease as said proteolytic enzyme, and calcium ion in a concentration of 5–250 mM/l.

13. A method of cleaning and disinfecting a contact lens according to claim 7, further comprising: rinsing said contact lens with a physiological isotonic solution after said contact lens was contacted with said cleaning and disinfecting solution; and immersing said contact lens in a fresh physiological isotonic solution.

14. A method of cleaning and disinfecting a contact lens according to claim 7, said contacting said contact lens with said cleaning and disinfecting solution for said short period of time is effected by rubbing said contact lens with said cleaning and disinfecting solution.

15. A method of cleaning and disinfecting a contact lens according to claim 7, wherein said contact lens is a soft contact lens.

* * * * *